United States Patent [19]

Chiarino et al.

[11] Patent Number: 5,028,626
[45] Date of Patent: Jul. 2, 1991

[54] PEPTIDES WITH PHARMACEUTICAL ACTIVITY

[75] Inventors: Dario Chiarino, Monza; Angelo Carenzi, Busto Arsizio; Davide Della Bella, Milan; Franco Pellacini, Sesto S. Giovanni, all of Italy

[73] Assignee: Zambon Group S.p.A., Vicenza, Italy

[21] Appl. No.: 322,890

[22] Filed: Mar. 15, 1989

[30] Foreign Application Priority Data

Mar. 16, 1988 [IT] Italy ................. 19790 A/88

[51] Int. Cl.$^5$ ........................... C07C 229/40
[52] U.S. Cl. ..................... 514/562; 562/430
[58] Field of Search ............ 514/19, 18, 562; 530/331; 564/162; 562/430

[56] References Cited

U.S. PATENT DOCUMENTS 4,185,156  1/1980  Umezawa et al. .
4,473,554  9/1984  Umezawa et al. ............. 530/331
4,883,808  11/1989 Foder .

FOREIGN PATENT DOCUMENTS 2393788 of 0000 France .

OTHER PUBLICATIONS

Journal of Medicinal Chemistry, vol. 20, No. 4, Apr. 1977.
Journal of Antiobiotics, vol. XXXIII, 1980.
Morrison et al., *Organic Chemistry*, 1973, p. 1173.
Poulson et al., *Organic Chemistry*, 1980, pp. 1025–1031.
Aoyagi et al., *J. App. Biochem.*, 1984, 6, pp. 212–221.

*Primary Examiner*—Lester L. Lee
*Assistant Examiner*—Stephen B. Maebius
*Attorney, Agent, or Firm*—Stevens, Davis, Miller & Mosher

[57] ABSTRACT

Compounds of formula

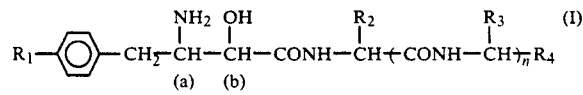

wherein $R_1$, $R_2$, $R_3$, $R_4$, and $\underline{n}$ have the meanings reported in the specification, processes for their preparation and pharmaceutical compositions containing them as active ingredient are described. The compounds of formula I are inhibitors of enzymatic systems and they are useful in pharmaceutical field.

6 Claims, No Drawings

PEPTIDES WITH PHARMACEUTICAL ACTIVITY

The present invention relates to peptide compounds and to their reduction products with inhibitory activity of enzymatic systems and, more particularly, it relates to amides of $\beta$-amino-butyric acid, to processes for their preparation and to pharmaceutical compositions containing them as active ingredient.

The drugs with activity on enzymatic systems represent a therapeutic class of recent development and of particular interest for its potential use in the pharmacological field in the treatment of immunodeficiency diseases, chronic infective diseases and diseases of tumoral origin.

Several natural as well as synthetic drugs have been studied; among these Levamisole (Merck Index 10th Ed., No. 9055, page 1321), Isoprinosin (Merck Index 10th Ed., No. 4859, page 722) and, more recently, Bestatin [Drug of the future, vol. VI, No. 10 (1981), page 604].

In particular, this last compound, whose chemical name is [(2S,3R)-3-amino-2-hydroxy-4-phenyl-butanoyl]-L-leucine, was isolated, the first time, from a culture of Streptomyces olivoreticuli (British Pat. No. 1510323- Zaidan Hojin Biseibutsu). Afterwards, Bestatin has been extensively studied as far as the structure-activity relationship is concerned.

For this purpose several derivatives substituted on the phenyl group were prepared but their activity resulted pratically always less than that of Bestatin [(R. Nishizawa and T. Saino in J. Med. Chem., vol. 20, (1977), No. 4, pages 510–515)].

We have now surprisingly found that compounds with a structure similar to that of Bestatin but wherein the phenyl is substituted on para position with sulfur containing groups show in vitro a pharmacological activity substantially equal to that of Bestatin but they show to be more resistant to metabolism in vivo and therefore they have a prolonged duration of activity.

Therefore object of the present invention are the compounds of formula

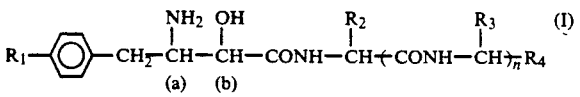

wherein
$R_1$ represents a mercapto, alkylthio, alkylsulfinyl or alkylsulfonyl group having from 1 to 6 carbon atoms in the alkyl moiety;
$R_2$ represents a sec.butyl or isobutyl group;
$R_3$ represents a hydrogen atom or a linear or branched $C_1$–$C_6$ alkyl optionally substituted by a hydroxy, mercapto, $C_1$–$C_3$ alkylthio, amino, carboxy, ureido group;
$\underline{n}$ represents 0 or 1;
$R_4$ represents a carboxy group or a group of formula —$COR_5$ wherein $R_5$ represents a $C_1$–$C_6$ alkoxy, an amino, mono or dialkylamino group having from 1 to 6 carbon atoms in the alkyl moiety; and when n=0 $R_4$ can be also a hydroxymethyl or a formyl group;
the carbon atoms marked by (a) and (b) are in R or S configuration.

The compounds of formula I have an inhibitory activity of enzymatic systems and they are useful in therapy in the treatment of immunodeficiency disorders, diseases of tumoral origin, muscular dystrophy and in the enhancement of analgesia induced by opioids. In particular, contrary to what reported in literature for related compounds [Takaaki Aoyagy et al., J. Appl. Biochem., 6, 212–221, (1984)] also the compounds of formula I wherein the carbon atom marked by (b) is in R configuration show interesting pharmacological properties, particularly a remarkable immunostimulating activity.

Preferred compounds of formula I are those wherein:
$R_1$ represents a mercapto, methylthio, ethylthio, methylsulfinyl, ethylsulfinyl, methylsulfonyl or ethylsulfonyl group;
$R_2$ represents a isobutyl group;
$\underline{n}$ is 0 and
$R_4$ represents carboxy.

The compounds of formula I can have at least one asymmetric centers, in addition to those marked by (a) and (b), and they can be in the form of stereoisomers.

Object of the present invention are the compounds of formula I in the form of stereoisomeric mixtures as well as in the form of single stereoisomers, preparable by separation from the stereoisomeric mixture according to conventional methods or by stereoselective synthesis.

A further object of the present invention are the salts of the compounds of formula I with pharmaceutically acceptable acids or, when $R_4$ represents a carboxy group or other acidic functions are present in the molecule, with pharmaceutically acceptable bases. Examples of suitable acids are hydrochloric, hydrobromic, benzoic, 4-hydroxybenzoic, tartaric, succinic, acetic, sulfuric, sulfonic, fumaric, hydriodic, glycolic, citric, maleic and phosphoric acid. Examples of suitable bases are sodium or potassium hydroxides, carbonates or bicarbonates, calcium or magnesium hydroxides, ethanolamine, 2-hydroxymethyl-2-amino-1,3-propanediol, dimethylaminoethanol, benzathine, N-methyl-D-glucamine, ethylenediamine, arginine and lysine.

A further object of the present invention are the processes for the preparation of the compounds of formula I. The compounds of the present invention are prepared according to the following condensation reaction.

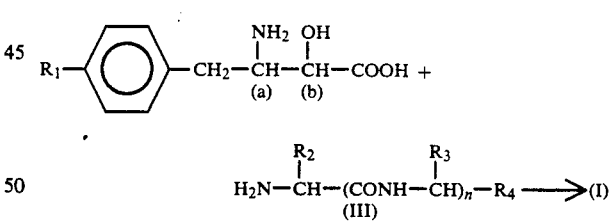

wherein $R_1$, $R_2$, $R_3$, $R_4$ and $\underline{n}$ have the above reported meanings; the carbon atoms marked by (a) and (b) have R or S configuration. The reaction is carried out according to techniques known in peptide chemistry by first protecting the secondary amino group of the compound of formula II and, then, by performing the condensation in the presence of a suitable condensing agent in an inert organic solvent, optionally in the presence of a base.

Suitable condensing agents are carbodiimides such as dicyclohexylcarbodiimide and 1-ethyl-3-(3-dimethylaminopropyl)-carbodiimide, optionally in the presence of N-hydroxy-benzotriazole.

The condensation reaction can be carried out also by using the mixed anhydride method, that is by preparing a mixed anhydride between the carboxy group of the compounds of formula II and an ester of a suitable organic acid such as ethylchloroformate or isobutylchloroformate, or by using reactive esters of the compounds of formula II such as, for example, cyanomethyl esters, vinyl esters, substituted or unsubstituted phenyl esters, thiophenyl esters or esters of N-hydroxy-succinimide or N-hydroxyphthalimide.

For the condensation reaction, suitable organic solvents are ethers such as ethyl ether, tetrahydrofuran or dioxane, esters such as ethyl acetate, ketones such as acetone or methylethylketone, chlorinated hydrocarbons such as methylenechloride or chloroform, amides or nitriles such as dimethylformamide, dimethylacetamide or acetonitrile, or mixtures thereof.

Examples of suitable bases are inorganic bases such as sodium bicarbonate and magnesium oxide or organic bases such as triethylamine and N-methyl-morpholine.

Suitable protecting groups for the amino group are t.butoxycarbonyl and benzyloxycarbonyl or the amino nitrogen can be protected as imide, for example as phthalimide.

Alternatively, the compounds of formula I wherein n=1 can be prepared also by condensation of a suitably protected compound of formula II with leucine or isoleucine and by subsequent further condensation with an aminoacid of formula

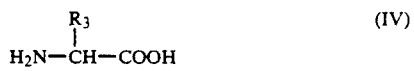

(IV)

wherein $R_3$ has the above reported meanings.

It is clear to the man skilled in the art that before carring out the condensation reactions it can be optionally necessary to protect the carboxy group of the intermediates of formula III and IV.

The protection is carried out by esterification, for example with methanol, ethanol or with substituted or unsubstituted benzyl alcohol.

The removal of the protective groups to obtain the compounds of formula I is carried out according to usual methods in peptide chemistry for example by catalytic hydrogenation, by saponification with bases, by acid hydrolysis with hydrobromic acid in acetic acid, with trifluoroacetic acid, with hydrochloric acid in solvents such as dioxane, tetrahydrofuran or ethyl acetate or with hydrofluoric acid or by hydrazinolysis.

From the compounds of formula I wherein $R_4$=COOH, then, by esterification with a suitable alcohol or by amidation with ammonia or a suitable amine, the compounds of formula I wherein $R_4$ represents a —$COR_5$ group are obtained.

Finally, by reduction of the compounds of formula I wherein $R_4$=COOH or —$COR_5$ (n=0) the compounds of formula I wherein $R_4$ represents a hydroxymethyl (—$CH_2OH$) or a formyl (CHO) group are obtained.

Alternatively, the compounds of formula I wherein $R_4$ is a $COR_5$, $CH_2OH$ or CHO group can be prepared directly by reaction of compounds of formula II with an amine of formula III wherein $R_4$ is a $COR_5$, $CH_2OH$ or CHO group, by condensation under conditions similar to those above described.

The compounds of formula II are preparable according to known methods such as, for example, the method described in the British Pat. No. 1510477 (Zaidan Hojin Biseibutsu) starting from the corrispondent cyanidrine.

The amines of formula III are known compounds or easily preparable according to known methods.

Examples of amine of formula III are leucine, isoleucine, their derivatives such as esters and amides or dipeptides obtained by condensation of leucine or isoleucine with an aminoacid of formula IV.

Example of aminoacids of formula IV are glycine, alanine, valine, leucine, isoleucine, serine, norvaline, norleucine, threonine, cysteine, methionine, aspartic acid, glutamic acid, arginine and lysine.

As above reported, the compounds of formula I have, in addition to the carbon atoms marked by (a) and (b) at least another asymmetric center.

The single stereoisomers can be separated from the stereoisomeric mixture according to known techniques by fractionated crystallization or by chromatography.

Alternatively the single stereoisomers can be prepared by stereo-selective synthesis using intermediates wherein the asymmetric centers have predetermined configuration.

The salts of the compounds object of the present invention with pharmaceutically acceptable acids or bases are preparable according to conventional techniques.

The compounds of formula I object of the present invention are able to competitively inhibit important enzymatic systems such as leucylaminopeptidases which is involved in the catabolism of endogenous peptides in mammals and to modulate immuno responses. Surprisingly, the compounds of formula I wherein the carbon atom marked by (b) is in R configuration, contrary to the 2R stereoisomers of Bestatin, are active and in particular show a remarkable immunostimulating activity.

These activities are equal or superior to that of Bestatin but the compounds object of the present invention show a greater bioavailability and a prolonged duration of activity because their half-time is longer.

The activity of the compounds of formula I has been evaluated as inhibitory effect on the activity of leucineaminopeptidase and as stimulating effect on the mitogenetic activity of mouse splenic lymphocytes.

The inhibitory effect of the tested compounds has been evaluated on a purified aminopeptidase obtained from hog kidney (Baehringer, 100U/mg).

The enzymatic activity was estimated spectrophotometrically by using L-leucinamide as substrate and by measuring the hydrolysis of the peptide bond as decrease of absorbance at 238 nm.

The enzyme was activated prior to assay at 37° C. for 2 hours, in the presence of $MgCl_2$ 1 mM and tris-HCl buffer 20 mM pH 8.5 in a total volume of 2.5 ml.

The enzymatic reaction was followed at 238 nm for at least 30 minutes at 25° C. in 2.5 ml of an incubation medium containing 50 µg of enzyme, leucineamide 50 mM, tris-HCl buffer 20 mM pH 8.5 and $MgCl_2$ 5 mM in the absence or in the presence of increasing concentrations of the tested compound.

The inhibitory effect was expressed as the concentration of the compound inducing a 50% decrease of the enzymatic activity ($IC_{50}$, nmoles/l).

The compounds of examples 3 and 11 showed an $IC_{50}$ of 10 and 11 nmoles/l respectively.

The immunostimulating activity has been evaluated as ability to stimulate the incorporation of $^3H$-timidine ($^3H$-TMD) in a culture of mouse splenic lymphocytes.

The splenic cells were drawn form C3H/H2 mice (age: 6–8 weeks) and suspended in RPMI-1640 medium containing HEPES 20 mM and 10% bovine fetal serum (inactivated to heat) at the concentration of $5 \times 10^6$ cells/ml.

Cells were sowed of Microtest plates (Falcon 3072) in the absence and in the presence of different concentrations of the compounds of formula I in a volume of 0.2 ml of medium.

After an incubation period of 48 hours at 37° C. in humidified environment at 5% $CO_2/O_2$, 0.5 microCi of $^3$H-TMD (specific activity 2 Ci/mmoles) were added and the incubation was protracted for further 24 hours.

Cells were collected by filtration (Tretertek Cell Harnester) and the incorporated radioactivity was measured by Packard TRI-CARB 4530 scintillator.

The mitogenetic effect was expressed as percentage increase in the incorporation of $^3$H-TMD in lymphocytes incubated with the compounds of formula I at the concentration of 1 μM with respect to the basal incorporation value.

The compound of Example 4 showed a (109%) percentage increase of $^3$H-TMD in lymphocytes.

The therapeutic uses of the compounds of formula I concern the treatment of pathologies with require an action on the immuno system such as those related to immunodepression or autoimmuno activity or in the presence of tumoral neoformations, preventing the appearance of muscular distrophies, inducing analgesia or enhancing the analgesia induced by an increased release of morphine-like endogenous peptides.

A further object of the present invention are the pharmaceutical compositions containing the compounds of formula I or their pharmaceutically acceptable salts as active ingredient.

These compositions can contain the active ingredient together with suitable pharmaceutical solid or liquid excipients and they can be administered by oral or parenteral route.

The doses of the compounds of formula I will vary depending on the route of administration and the selected pharmaceutical preparation but they are between 10 mg and 1000 mg a day.

The pharmaceutical preparation, preparable according to conventional techniques, can be solid such as tablets, coated tablets, capsules, powders, granulates or liquid such as solutions, suspensions, emulsions.

In addition to the usual excipients, the compositions object of the present invention may contain also preserving agents, stabilizing agents, wetting agents, emulsifiers, salts in order to regulate the osmotic pressure, buffers, colouring agents, flavouring agents.

In order to better illustrate the present invention without limiting it, the following examples are now given.

EXAMPLE 1

Preparation of N-[(2S,3R)-3-benzyloxycarbonylamino-2-hydroxy-4-(4-methylsulfonyl-phenyl)-butanoyl]-L-leucine benzyl ester Triethylamine (30.6 ml; 0.220 mmoles) was added dropwise, at +10° C. and under stirring, to a suspension of [(2S,3R)-3-benzyloxycarbonylamino-2-hydroxy-4-(4-methylsulfonyl-phenyl)]-butanoic acid (81.26 g; 0.199 moles), (m.p. 168°-172° C.) prepared according to the method described in British Pat. No. 1510477, L-leucine benzylester p.toluenesulfonate (86.57 g; 0.220 moles) and hydroxy benzotriazole (37 g; 0.274 moles) in a mixture of tetrahydrofuran (800 ml) and methylene chloride (200 ml).

To the obtained solution, a solution of dicyclohexylcarbodiimide (56.6 g; 0.274 moles) in methylene chloride (200 ml) was added, always at 10° C.

The reaction mixture was kept under stirring at room temperature for 18 hours, then it was filtered and evaporated to dryness under reduced pressure.

The residue was dissolved in methylene chloride (500 ml) and treated, first, with a 5% hydrochloric acid solution and, then, with a 5% sodium bicarbonate solution.

The organic phase, after drying on sodium sulphate, was evaporated to dryness.

The residue was dissolved in ethyl ether and, after filtration, the ether solution was evaporated to dryness under reduced pressure.

A crude (117.8 g) was obtained and crystallized from methanol (1 l) giving N-[(2S,3R)-3-benzyloxycarbonylamino-2-hydroxy-4-(4-methylsulfonyl-phenyl)-butanoyl]-L-leucine benzyl ester (96 g; 79% yield) with m.p. 145°-147° C.

$[\alpha]_D^{20} = +30.8°$ (c=1%, DMF)

$^1$H-NMR (200 MHz, CD$_3$OD-TMS): delta (ppm): 7.68(AA'BB' system 4H); 7.38-7.19(m, 10H); $\nu_A$=5.07-$\nu_B$=5.04(ABq, $J_{AB}$=12.4 Hz, 2H); $\nu_A$=5.02-$\nu_B$=4.83(ABq, $J_{AB}$=12.5 Hz, 2H); 4.65-4.55(m, 1H); 4.29(m, 1H); 4.06(d, 1H, J=2.4 Hz); 3.06(s, 3H); 3.01-2.88(m, 2H); 1.72-1.54(m, 3H), 0.86(d, 3H, J=6.5 Hz); 0.82(d, 3H, J=7.0 Hz).

EXAMPLE 2

Preparation of N-[(2R,3S)-3-benzyloxycarbonylamino-2-hydroxy-4-(4-methylsulfonyl-phenyl)-butanoyl]-L-leucine benzyl ester By working in a way similar to that described in Example 1 and using (2R,3S)-3-benzyloxycarbonylamino-2-hydroxy-4-(4-methylsulfonyl-phenyl)-butanoic acid (8.5 g; 0.021 moles) as starting compound, N-[(2R,3S)-3-benzyloxycarbonylamino-2-hydroxy-4-(4-methylsulfonyl-phenyl)-butanoyl]-L-leucine benzyl ester (9.4 g; 73% yield) was obtained with m.p. 136°-138° C.

$[\alpha]_D^{20} = -54.4°$ (c=1%, DMF)

$^1$H-NMR (200 MHz, DMSO-d$_6$+D$_2$O-TMS): delta (ppm): 8.24(d, J=7.8 Hz, 1H); 7.82-7.15(m, 9H); 6.91(d, J=9.2 Hz, 1H); 5.08(s, 2H); $\nu_A$=4.81-$\nu_B$=4.90(ABq, $J_{AB}$=12.9 Hz, 2H); 4.32(m, 1H); 4.13-4.00(m, 1H); 3.93(d, J=3.4 Hz, 1H); 3.14(s, 3H); 2.99-2.69(m, 2H); 1.76-1.42(m, 3H); 0.82(d, J=6.0 Hz, 3H); 0.76(d, J=5.9 Hz, 3H).

EXAMPLE 3

Preparation of N-[(2S,3R)-3-amino-2-hydroxy-4-(4-methylsulfonyl-phenyl)-butanoyl]-L-leucine To a solution of N-[(2S,3R)-3-benzyloxycarbonylamino-2-hydroxy-4-(4-methylsulfonyl-phenyl)-butanoyl]-L-leucine benzyl ester (40 g; 0.065 moles), prepared as described in Example 1, in acetic acid (270 ml) 10% palladium on activated charcoal (4 g) was added. The suspension was hydrogenated under pressure (about 3 atm.) in a Parr apparatus at room temperature.

At the end of hydrogen absorption, the suspension was filtered. After evaporation to dryness under reduced pressure, the residue was dissolved in water and evaporated again.

The crude was triturated in acetone, filtered and dried under vacuo at 50° C. on $P_2O_5$.

N-[(2S,3R)-3-amino-2-hydroxy-4-(4-methylsulfonyl-phenyl)-butanoyl]-L-leucine (46.31 g; 92% yield) with m.p. 242°-244° C. (dec.) was obtained.

$[\alpha]_D^{20} = -15.1°$ (c=1%, HCl 0.1N)

$^1$H-NMR (200 MHz, DCl 1N in $D_2O$-TSP): delta (ppm): 7.98-7.60(m, 4H); 4.39-4.34(m, 1H); 4.33(d, 1H, J=4.6 Hz); 3.99-3.90(m, 1H); 3.35-3.08(m, 2H); 3.27(s, 3H); 1.80-1.59(m, 3H); 0.93(d, 3H, 3.35-3.08(m, 2H); 3.27(s, 3H); 1.80-1.59(m, 3H); 0.93(d, 3H, J=6.2 Hz); 0.89(d, 3H, J=6.2 Hz).

EXAMPLE 4

Preparation of
N-[(2R,3S)-3-amino-2-hydroxy-4-(4-methylsulfonyl-phenyl)-butanoyl]-L-leucine By working in a way similar to that described in Example 3 and using N-[(2R,3S)-3-benzyloxycarbonylamino-2-hydroxy-4-(4-methylsulfonyl-phenyl)-butanoyl]-L-leucine benzyl ester (3.42 g; 0.0056 moles), prepared as described in Example 2, as starting compound, N-[(2R,3S)-3-amino-2-hydroxy-4-(4-methylsulfonyl-phenyl)-butanoyl]-L-leucine (1.13 g; 52% yield) was obtained.

m.p. 239°-241° C. (dec.)

$[\alpha]_D^{20} = -7.8°$ (c=1%, HCl 0.1N)

$^1$H-NMR (200 MHz, DCl 1N in $D_2O$-TSP): delta (ppm): 8.03-7.66(m, 4H); 4.47-4.42(m, 1H); 4.32(d, J=3.8 Hz, 1H); 4.08-3.96(m, 1H); 3.40-3.19(m, 2H); 3.31(s, 3H); 1.90-1.58(m, 3H); 0.95(d, J=6.2 Hz, 3H); 0.90(d, J=6.0 Hz, 3H).

EXAMPLE 5

Preparation of
N-[(2S)-1-hydroxy-4-methyl-2-pentyl]-(2S,3R)-3-benzyloxycarbonylamino-2-hydroxy-4-(4-methylsulfonyl-phenyl)-butanamide A solution of dicyclohexylcarbodiimide (4.1 g; 0.02 moles) in methylene cloride (15 ml) was added dropwise, under stirring at +10° C., to a solution of (2S,3R)-3-benzyloxycarbonylamino-2-hydroxy-4-(4-methylsulfonyl-phenyl)butanoic acid (7.2 g; 0.0176 moles), L-leucinol (2.5 ml; 0.02 moles) in tetrahydrofuran (70 ml) and methylene chloride (18 ml).

After 18 hours under stirring at room temperature and filtration, the solution was evaporated to dryness under reduced pressure. The residue was dissolved in methylene chloride and the organic solution was washed with a 5% hydrochloric acid solution and, then, with a 5% sodium bicarbonate solution.

From the organic phase, after drying on sodium sulphate and evaporation of the solvent under reduced pressure, a crude (8.1 g) was obtained and purified by chromatography on silica gel (eluent ethyl acetate: methanol=95:5) giving N-[(2S)-1-hydroxy-4-methyl2-pentyl]-(2S,3R)-3-benzyloxycarbonylamino-2-hydroxy-4-(4-methylsulfonyl-phenyl)-butanamide (4.7 g; 52.7% yield) with m.p. 165°-173° C.

$[\alpha]_D^{20} = +34.5°$ (c=1%, DMF)

$^1$H-NMR (200 MHz, $CD_3OD$-TMS): delta (ppm): 7.69(AA'BB' system, 4H); 7.39-7.21(m, 5H); $\nu_A$=5.34-$\nu_B$=4.53(ABq, $J_{AB}$=12.6 Hz, 2H); 4.36-4.27(m, 1H); 4.07-3.95(m, 1H); 4.04(d, 1H, J=2.2 Hz); 3.47(d, 2H, J=5.3 Hz); 3.10-2.90(m, 2H); 3.06(s, 3H); 1.69-1.21(m, 3H); 0.87(d, 3H, J=6.6 Hz); 0.85(d, 3H, J=6.5 Hz).

EXAMPLE 6

Preparation of
N-[(2S)-1-hydroxy-4-methyl-2-pentyl]-(2S,3R)-3-amino-2-hydroxy-4-(4-methylsulfonyl-phenyl)-butanamide hydrochloride A solution of N-[(2S)-1-hydroxy-4-methyl-2-pentyl]-(2S,3R)-3-benzyloxycarbonylamino-2-hydroxy-4-(4-methylsulfonyl-phenyl)-butanamide (4.6 g; 0.009 moles), prepared as described in example 5, in acetic acid was hydrogenated as described in example 3.

N-[(2S)-1-hydroxy-4-methyl-2-pentyl]-(2S,3R)-3-amino-2-hydroxy-4-(4-methylsulfonyl-phenyl)-butanamide (3.4 g) was obtained and dissolved in ethyl acetate (50 ml).

To this solution hydrochloric acid in ether was added and the precipitate was filtered, washed with ethyl ether, dried and cristallized from acetonitrile (50 ml) giving N-[(2S)-1-hydroxy-4-methyl-2-pentyl]-(2S,3R)-3-amino-2-hydroxy-4-(4-methylsulfonylphenyl)-butanamide hydrochloride (2.5 g; 67.9% yield) with m.p. 214°-216° C. (dec.).

$[\alpha]_D^{20} = -3.3°$ (c=1%, $H_2O$)

$^1$H-NMR (200 MHz, DCl 1N in $D_2O$-TSP): delta (ppm): 7.99-7.58(m, 4H); 4.281(d, 1H, J=4.9 Hz); 4.03-3.87(m, 2H); 3.27(s, 3H); 3.33-3.04(m, 2H); $\nu_A$=3.59-$\nu_B$=3.47(AB portion of an ABX system, $J_{AB}$=11.5 Hz, $J_{AX}$=4.4 Hz, $J_{BX}$=7.0 Hz, 2H); 1.67-1.44(m, 1H); 1.42-1.32(m, 2H); 0.88(d, 3H, J=6.2 Hz); 0.86(d, 3H, J=6.2 Hz).

EXAMPLE 7

Preparation of
N-[(2S,3R)-3-benzyloxycarbonylamino-2-hydroxy-4-(4-methylthio-phenyl)-butanoyl]-L-leucine methyl ester A solution of (2S,3R)-3-benzyloxycarbonylamino-2-hydroxy-4-(4-methylthio-phenyl)-butanoic acid (2.8 g; 0.0074 moles), (m.p. 174°-177° C.), prepared according to the method described in British Pat. No. 1510477, L-leucine methyl ester hydrochloride (1.47 g; 0.00812 moles) and hydroxybenzotriazole (1.37 g; 0.0102 moles) in tetrahydrofuran (36 ml) was cooled at +10° C.

A suspension was obtained to which triethylamine (1.13 ml; 0.00812 moles) and, then, a solution of dicyclohexylcarbodiimide (2.1 g; 0.0102 moles) in methylene chloride (7 ml) were added, keeping the temperature at +10° C. and under stirring.

The reaction mixture was kept under stirring overnight at room temperature and it was filtered.

The organic solution was evaporated to dryness under reduced pressure and the residue was dissolved in ethyl acetate (20 ml). The solution was, then, washed with a 5% hydrochloric acid solution (20 ml), with water and, finally, with a 5% sodium bicarbonate solution.

The organic phase, after drying on sodium sulphate, was evaporated to dryness under reduced pressure. A solid (4.5 g) was obtained and crystallized from ethanol (35 ml) giving [(2S,3R)-3-benzyloxycarbonylamino-2-hydroxy-4-(4-methylthio-phenyl)-butanoyl]-L-leucine methyl ester (2.96 g; 79% yield) with m.p. 130°-132° C.

$[\alpha]_D^{20} = +38.9°$ (c=1%, DMF)

$^1$H-NMR (200 MHz, $CD_3OD$-TMS): delta (ppm): 7.37-7.08(m, 9H); $\nu_A$=5.07-$\nu_B$=4.86(ABq, $J_{AB}$=12.6 Hz, 2H); 4.59-4.51(m, 1H); 4.27-4.18(m, 1H); 4.03(d, 1H, J=2.3 Hz); 3.69(s, 3H); $\nu_A$=2.88-$\nu_B$=2.81(AB portion of an ABX system, $J_{AB}$=13.5 Hz, $J_{AX}$=7.0 Hz, $J_{BX}$=8.2 Hz, 2H); 2.43(s, 3H); 1.77-1.52(m, 3H); 0.84(d, 3H, J=6.1 Hz); 0.83(d, 3H, J=6.1 Hz).

EXAMPLE 8

Preparation of
N-[(2R,3S)-3-benzyloxycarbonylamino-2-hydroxy-4-(4-methylthio-phenyl)-butanoyl]-L-leucine methyl ester By working in a way similar to that described in Example 7 and using (2R,3S)-3-benzyloxycarbonylamino-2-hydroxy-4-(4-methylthiophenyl)-butanoic acid (2.4 g; 0.0064 moles) as starting compound, N-[(2R,3S)-3-benzyloxycarbonylamino-2-hydroxy-4-(4-methylthiophenyl)butanoyl]-L-leucine methyl ester (3.1 g; 96% yield) was obtained.

m.p. 146°-150° C.

$[\alpha]_D^{20}$= +22.9° (c=1%, DMF)

$^1$H-NMR (200 MHz, DMSO-d$_6$+D$_2$O-TMS): delta (ppm): 8.07(d, J=8.2 Hz, 1H); 7.36-7.00(m, 10H); $\nu_A$=4.94-$\nu_B$=4.87(ABq, $J_{AB}$=12.9 Hz, 2H); 4.33(m, 1H); 4.03-3.88(m, 2H); 3.6(s, 3H); 2.71-2.56(m, 2H); 2.4(s, 3H); 1.78-1.40(m, 3H); 0.85(d, J=6.2 Hz, 3H); 0.82(d, J=6.2 Hz, 3H).

EXAMPLE 9

Preparation of
N-[(2S,3R)-3-benzyloxycarbonylamino-2-hydroxy-4-(4-methylthio-phenyl)-butanoyl]-L-leucine To a solution of N-[(2S,3R)-3-benzyloxycarbonylamino-2-hydroxy-4-(4-methylthio-phenyl)-butanoyl]-L-leucine methyl ester (4.5 g; 0.00887 moles), prepared as described in example 7, in methanol (140 ml), a 1N solution of sodium hydroxide (9.2 ml) was added at 0° C. and under stirring.

The reaction mixture was kept under stirring at room temperature for 20 hours, then methanol was evaporated under reduced pressure and the residue was shared among water (50 ml) and ethyl acetate (50 ml). The mixture was acidified with hydrochloric acid up to pH 1 and phases were separated.

After drying on sodium sulphate, the organic phase was evaporated to dryness under reduced pressure and the residue was crystallized from acetonitrile (140 ml) giving N-[(2S,3R)-3-benzyloxycarbonylamino-2-hydroxy-4-(4-methylthio-phenyl)-butanoyl]-L-leucine (3.32 g; 7.6% yield) with m.p. 180°-182° C.

$[\alpha]_D^{20}$= +40.5° (c=1%, DMF)

$^1$H-NMR (200 MHz, CD$_3$OD-TMS): delta (ppm): 7.38-7.07(m, 9H); $\nu_A$=5.08$\nu_B$=4.86(ABq, $J_{AB}$=12.6 Hz, 2H); 4.55-4.48(m, 1H); 4.30-4.16(m, 1H); 4.03(d, 1H, J=2.2 Hz); 2.44(s, 3H); $\nu_A$=2.89-$\nu_B$=2.81(AB portion of an ABX system, $J_{AB}$=13.3 Hz, $J_{AX}$=6.0 Hz, $J_{BX}$=7.2 Hz, 2H); 1.77-1.53(m, 3H); 0.88(d, 3H, J=6.5 Hz); 0.85(d, 3H, J=6.5 Hz).

EXAMPLE 10

Preparation of
N-[(2R,3R)-3-benzyloxycarbonylamino-2-hydroxy-4-(4-methylthio-phenyl)-butanoyl]-L-leucine By working in a way similar to that described in Example 9 and using N-[(2R,3R)-3-benzyloxycarbonylamino-2-hydroxy-4-(4-methylthio-phenyl)-butanoyl]-L-leucine methyl ester (3 g; 0.0059 moles) as starting compound, N-[(2R,3R)-3-benzyloxycarbonylamino-2-hydroxy-4-(4-methylthio-phenyl)-butanoyl]-L-leucine (1.64 g; 56% yield) was obtained.

m.p. 170°-172° C. (dec.)

$[\alpha]_D^{20}$= +27.8° (c=1%, DMF)

$^1$H-NMR (200 MHz, DMSO-d$_6$+D$_2$O-TMS): delta (ppm): 7.90(d, J=8.2 Hz, 1H); 7.37-7.01(m, 9H); $\nu_A$=4.94-$\nu_B$=4.88(ABq, $J_{AB}$=12.8 Hz, 2H); 4.26(m, 1H); 4.03-3.90(m, 2H); 2.75-2.56(m, 2H); 2.41(s, 3H); 1.76-1.40(m, 3H); 0.86(d, J=6.6 Hz, 3H); 0.83(d, J=6.6 Hz, 3H).

EXAMPLE 11

Preparation of
N-[(2S,3R)-3-amino-2-hydroxy-4-(4-methylthio-phenyl)-butanoyl]-L-leucine hydrobromide To a suspension of N-[(2S,3R)-3-benzyloxycarbonylamino-2-hydroxy-4-(4-methylthio-phenyl)-butanoyl]-L-leucine (2.69 g; 0.0055 moles) in acetic acid (10.8 ml), at room temperature and under stirring, 33% hydrobromic acid (5.38 ml) was added.

After 10 minutes the reaction mixture was poured into ethyl ether (800 ml) and the so obtained precipitate was filtered. A crude (1.78 g) was obtained and crystallized from a mixture of acetonitrile (250 ml) and water (5 ml) giving N-[(2S,3R)-3-amino-2-hydroxy-4-(4-methylthio-phenyl)-butanoyl]-L-leucine hydrobromide (1.07 g; 44.7% yield) with m.p. 190°-195° C. (dec.).

$[\alpha]_D^{20}$= +6.1° (c=1%, DMF)

$^1$H-NMR (200 MHz, CD$_3$OD-TMS): delta (ppm): 10.22(s, 1H); 8.28(d, 1H); 7.88(bs, 2H); 7.25(AA'BB' system, 4H); 4.46(m, 1H); 4.01(m, 1H); 4.29-4.18(m, 1H); $\nu_A$=2.92-$\nu_B$=2.75(AB portion of an ABX system, $J_{AB}$=13.7 Hz, $J_{AX}$=14.1 Hz, $J_{BX}$=13.7 Hz, 2H); 2.48(s, 3H); 1.74-1.46(m, 3H); 0.91(d, 3H, J=5.7 Hz); 0.89(d, 3H, J=5.7 Hz).

EXAMPLE 12

Preparation of
N-[(2R,3R)-3-amino-2-hydroxy-4-(4-methylthio-phenyl)-butanoyl]-L-leucine hydrobromide By working in a way similar to that described in Example 11 and using N-[(2R,3R)-3-benzyloxycarbonylamino-2-hydroxy-4-(4-methylthio-phenyl)-butanoyl]-L-leucine (1.3 g; 0.0026 moles) as starting compound, N-[(2R,3R)-3-amino-2-hydroxy-4-(4-methylthiophenyl)-butanoyl]-L-leucine hydrobromide (0.37 g; 33% yield) was obtained.

m.p. 235°-238° C. (dec.)

$[\alpha]_D^{20}$= +23.15° (c=1%, DMF)

$^1$H-NMR (200 MHz, DMSO-d$_6$+D$_2$O-TMS): delta (ppm): 7.20-7.08(m, 4H); 4.27(d, J=2.9 Hz, 1H); 4.21-4.14(m, 1H); 3.60-3.52(m, 1H); 2.89-2.62(m, 2H); 2.41(s, 3H); 1.70-1.49(m, 3H); 0.86(d, J=5.9 Hz, 3H); 0.82(d, J=5.9 Hz, 3H).

What we claim is

1. A compound selected from the group consisting of:
   N-[(2S,3R)-3-amino-2-hydroxy-4-(4-methylsulfonyl-phenyl)-butanoyl]-L-leucine;
   N-[(2R,3S)-3-amino-2-hydroxy-4-(4-methylsulfonyl-phenyl)-butanoyl]-L-leucine;
   N-[(2S,3R)-3-amino-2-hydroxy-4-(4-methylthio-phenyl)-butanoyl]-L-leucine; and
   N-[(2R,3R)-3-amino-2-hydroxy-4-(4-methylthio-phenyl)-butanoyl]-L-leucine,
   or a pharmaceutically acceptable salt thereof.

2. N-[(2S,3R)-3-amino-2-hydroxy-4-(4-methylsulfonylphenyl)-butanoyl]-L-leucine, or a pharmaceutically acceptable salt thereof.

3. N-[(2R,3S)-3-amino-2-hydroxy-4-(4-methylsulfonylphenyl)-butanoyl]-L-leucine, or a pharmaceutically acceptable salt thereof.

4. N-[(2S,3R)-3-amino-2-hydroxy-4-(4-methylthiophenyl)-butanoyl]-L-leucine, or a pharmaceutically acceptable salt thereof.

5. N-[(2R,3R)-3-amino-2-hydroxy-4-(4-methylthiophenyl)-butanoyl]-L-leucine, or a pharmaceutically acceptable salt thereof.

6. A pharmaceutical composition containing a compound according to claim 11 as active ingredient and a carrier suitable for pharmaceutical use.

* * * * *